United States Patent [19]
Yanagi et al.

[11] Patent Number: 4,893,320
[45] Date of Patent: Jan. 9, 1990

[54] APPARATUS FOR COUNTING PARTICLES ATTACHED TO SURFACES OF A SOLID

[75] Inventors: Motonori Yanagi; Masaharu Hama; Nobuyoshi Hattori; Takaaki Fukumoto, all of Itami, Japan

[73] Assignee: Mitsubishi Denki Kabushiki Kaisha, Japan

[21] Appl. No.: 246,743

[22] Filed: Sep. 20, 1988

[30] Foreign Application Priority Data

Jun. 8, 1988 [JP] Japan .................. 63-139540

[51] Int. Cl.⁴ .................. G01N 15/10; G01N 29/02; B08B 3/12
[52] U.S. Cl. .................. 377/11; 134/184
[58] Field of Search .................. 310/17, 19; 377/10, 377/11; 134/184; 68/355

[56] References Cited

U.S. PATENT DOCUMENTS

| | | | |
|---|---|---|---|
| 3,830,969 | 8/1974 | Hofstein | 377/10 |
| 4,409,999 | 10/1983 | Pedziwiatr | 134/184 |
| 4,618,263 | 10/1986 | McCord | 134/184 |
| 4,710,021 | 12/1987 | von Behrens | 377/11 |
| 4,736,760 | 4/1988 | Coberly et al. | 134/184 |

Primary Examiner—John S. Heyman
Attorney, Agent, or Firm—Leydig, Voit & Mayer

[57] ABSTRACT

An apparatus for counting particles attached to surfaces of a solid is disclosed which includes an external tank, an internal tank disposed within the external tank for hermetically accommodating a measuring liquid into which a sample having particles attached to the surfaces thereof is to be immersed, a driving mechanism for rotating the internal tank with respect to the external tank, sonic wave generators provided on the external tank for generating sonic waves having a plurality of different frequencies toward the internal tank, and a measuring mechanism connectable to the internal tank in a hermetic fashion for counting the number of particles in the measuring liquid removed from the sample by the sonic waves generated from the sonic wave generators.

19 Claims, 3 Drawing Sheets

APPARATUS FOR COUNTING PARTICLES ATTACHED TO SURFACES OF A SOLID

BACKGROUND OF THE INVENTION

1. Field of the Invention:

The present invention relates to an apparatus for measuring the quantity of particles attached to a surfaces of solid by washing away the particles from the solid surfaces in a liquid and counting the particles contained in the liquid.

2. Description of the Prior Art:

FIG. 4 is a schematic view of a known apparatus for counting the particles attached to the surface of a solid. The apparatus includes a box-shaped measuring tank 1A which is open at the upper portion thereof and which is capable of accommodating a measuring liquid into which is immersed a sample such as a solid on the surface of which particles to be measured are attached, an ultrasonic wave generating device 2A provided at the bottom of the measuring tank 1A for generating ultrasonic waves having a single frequency, and a measuring means 3A, such as a known counter of dust particles in a liquid, disposed adjacent to the measuring tank 1A for counting particles in the measuring liquid contained in the measuring tank 1A. The measuring means 3A has a light source 3a disposed outside the measuring tank 1A and adjacent to one side thereof for radiating light having a constant wavelength, such as monochromatic light, toward the measuring tank 1A, and a light-receiving means 3b disposed at a predetermined angle to the light source 3a for receiving light which has been radiated from the light source 3a and scattered by the particles in the measuring liquid to thereby obtain from the quantity of light which has been received the number as well as the diameter of particles in the liquid contained in the measuring tank 1A.

The principle of counting the particles contained in the measuring liquid by the measuring means 3A will be described below. When a monochromatic light such as a laser beam radiates upon particles in a liquid, the intensity of light scattered by the particles is determined by (1) the diameter of the particles, (2) the wavelength of the light, (3) the index of refraction of light in the particles, and (4) the angle formed by the direction of incidence and the direction of scatter. If items (2) and (4) are fixed, the particle diameter becomes a one-valued function of the intensity of light scattered, and the particle diameter can be therefore unequivocally determined by measuring the intensity of the light scattered, the number of times the scattered light is detected representing the number of particles. In this way, the diameter and the number of dust or particles contained in the measuring liquid can be measured according to the above-described principle.

Next, the operation of the known apparatus for counting particles attached to the surfaces of a solid which is arranged in the above-described manner will be described. After the measuring tank 1A has been filled with a measuring liquid such as a clean liquid chemical or pure water, a sample such as a solid to be inspected is immersed therein, and ultrasonic cleaning thereof is then conducted by the actuation of the ultrasonic wave generating device 2A so as to wash away the particles attached to the surfaces of the sample in the measuring liquid. Subsequently, the sample is removed from the measuring tank 1, and a light beam such as visible light, a laser beam or ultraviolet light then irradiates the measuring liquid from the light source 3a, whereby the light strikes and is scattered by the particles in the measuring liquid, part of the light scattered being received by the light-receiving means 3b. Data representing the intensity of light received by the light-receiving means 3b as well as the number of times the light is radiated from the light source 3a is sent to a data processing device (not shown) where it is used to calculate the number of particles in the measuring liquid on the basis of the above-described principle and thereby to measure the quantity of particles which have been washed away from the sample in the measuring liquid.

Known ultrasonic cleaning of the sample is conducted using ultrasonic waves having a uniform frequency. Since the physical and chemical principles of cleaning may change when the frequency changes, the particles washed into the liquid may vary with the physical properties, the strength of attachment or by the size of the particles attached to the sample, and actual distribution of the particles on the surfaces of the sample may therefore differ from the particle size distribution of the particles measured in the measuring liquid.

Further, the measuring liquid is easily contaminated by dust which enters the measuring liquid from the ambient atmosphere during the process in which the particles attached to the surfaces of the solid are washed away in the measuring liquid or the process in which the particles contained in the measuring liquid are counted, easily generating measurement errors.

SUMMARY OF THE INVENTION

In view of the above-described problems of the prior art, an object of the present invention is to provide an apparatus for counting particles attached to the surfaces of a solid in which the contamination of a measuring liquid from the ambient atmosphere can be eliminated and which is capable of reproducing particle size distribution of the substance attached to the surface of a sample faithfully in the measuring liquid so that a highly reliable counting of particles which ensures a value which is very close to the absolute value of particles attached to the surface of the solid can be carried out.

To this end, the present invention provides an apparatus for counting particles attached to surfaces of a solid which comprises: an external tank; an internal tank disposed within the external tank, the internal tank being capable of accommodating in an airtight fashion a measuring liquid into which a sample having particles attached to the surfaces thereof is to be immersed, a driving means for rotating the internal tank with respect to the external tank, a sonic wave generating means provided on the external tank for generating sonic waves having a plurality of different frequencies directed toward the internal tank, and a measuring means connectable to the internal tank in an airtight fashion for counting the number of particles in the measuring liquid that have been removed from the sample by the sonic waves generated from the sonic wave generating means.

In the apparatus for counting particles attached to the surface of a solid according to the present invention, after the sample has been accommodated in the internal tank in an airtight fashion, sonic waves having a plurality of different frequencies irradiate the overall surfaces of the sample while the internal tank is being rotated relative to the external tank. In consequence, the particles attached to the surfaces of the sample can be evenly and very efficiently removed from the sample regardless of the frequency and the shape of the sample and can be washed away in the measuring liquid contained in the internal tank. Further, since the measuring liquid containing the particles removed from the sample can be transferred to the measuring means without being contaminated by the ambient atmosphere, reliability of particle measurement can be remarkably improved.

DETAILED DESCRIPTION OF THE PREFERRED EMBODIMENT

Figure 1:
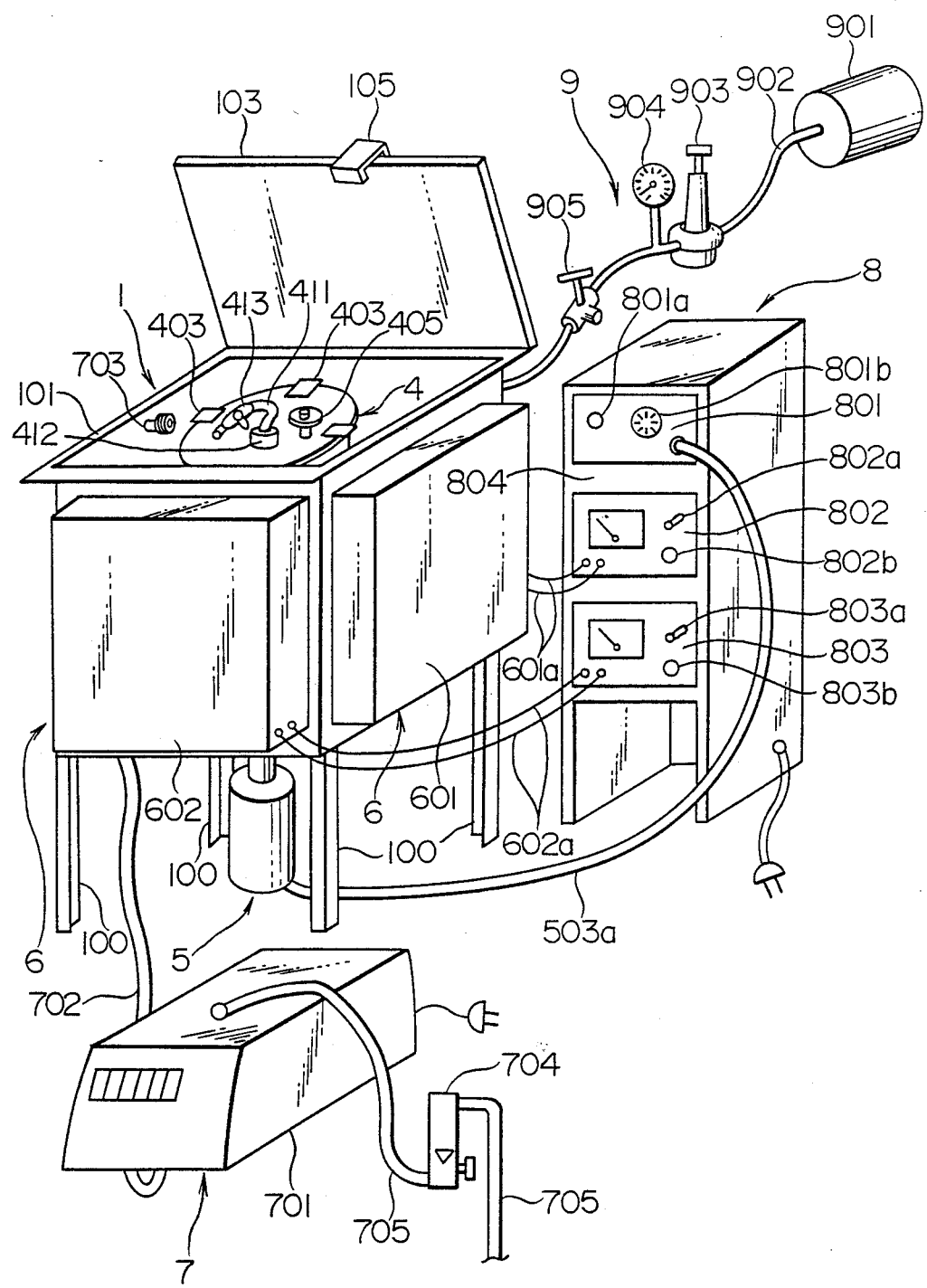
FIG. 1 is a schematic perspective view of an apparatus for counting particles attached to the surface of a solid, showing an embodiment of the present invention.

An embodiment of the present invention will be described below with reference to FIGS. 1 through 3. An apparatus for counting the particles attached onto the surfaces of an object shown in FIG. 1 includes an external tank 1, an internal tank disposed within the external tank 1 for accommodating a measuring liquid 3 into which a sample 2 is immersed to whose surfaces are attached particles to be measured, a driving means 5 for rotating the internal tank 4, a sonic wave generating means 6 provided on the external tank for generating sonic waves of a plurality of different frequencies including ultrasonic waves and megasonic waves, and a measuring means 7 for counting particles contained in the measuring liquid 3 which have been removed from the sample 2 by the sonic waves generated from the sonic wave generating means 6, the measuring means 7 being provided in such a manner that it can be connected to the internal tank 4 in an airtight fashion.

Figure 2:
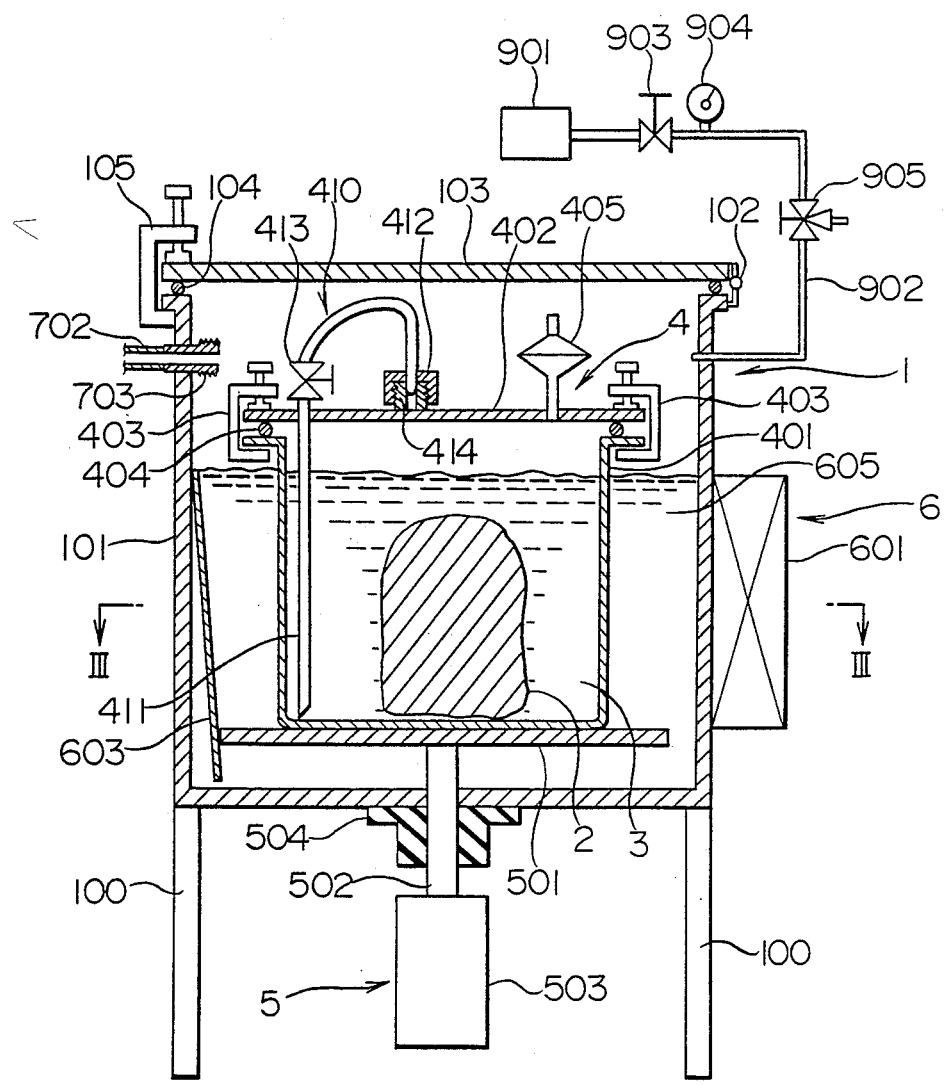
FIG. 2 is a front cross-sectional view of the essential parts of the apparatus of FIG. 1.
Figure 3:
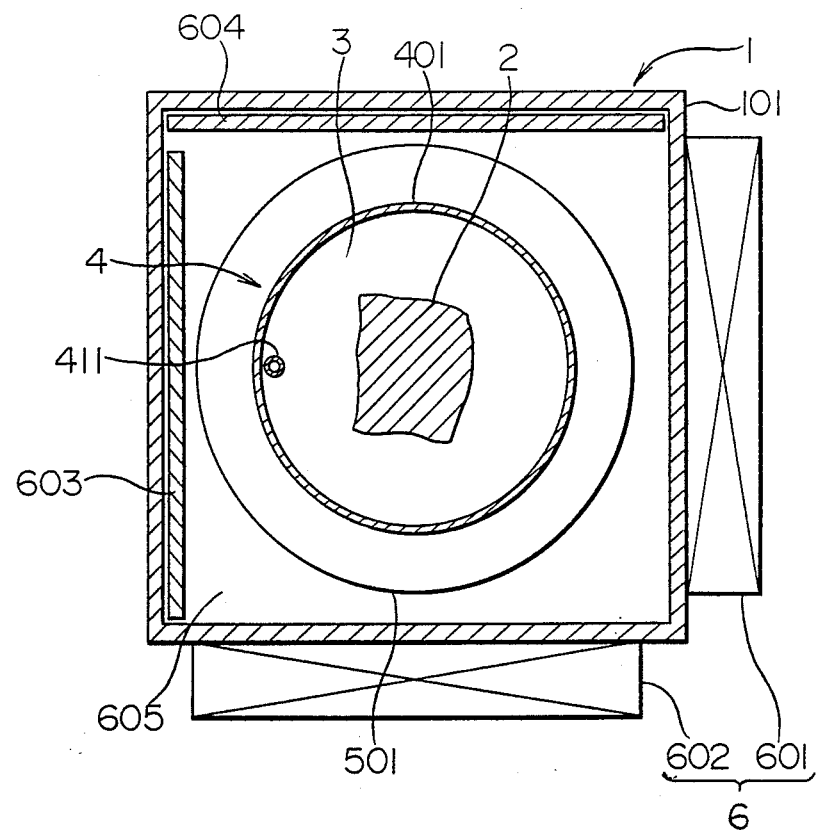
FIG. 3 is a cross-section taken along the line III—III of FIG. 2.

As will be apparent from FIGS. 2 and 3, the external tank 1 includes: a box-shaped container 101 which is open at the upper surface thereof and which is made of a material which sonic waves penetrate well, the container 101 being fixedly supported by a plurality of legs 100 on a floor (not shown); and a square outer lid 103 attached to one side of the open upper surface of the container 101 by a hinge 102. A packing 104 such as an O-ring is provided on either the inner surface of the outer lid 103 or the upper edge of the container 101. On the side edge of the outer lid 103 which faces the hinged side edge thereof is provided a fastener 105 which fixes the outer lid 103 to the upper end of the container 101 in an airtight fashion with the packing 104 interposed therebetween when the outer lid 103 is closed.

The internal tank 4 includes, a container 401 in the form of a cylinder having an open top and a closed bottom, and an inner lid 402 detachably provided on the open upper surface of the container 401. The container 401 is made of a material to which particles do not easily adhere and which does not generate dust. For example, the container 401 is made of quartz, glass, silicon, Teflon, SUS or polymeric polypropylene. The inner lid 402 is made of a firm material to which particles do not easily adhere. The lid 402 is made of thick glass plate, SUS plate, or plastic plate. In particular, a portion of the cylindrical container 401 which is radiated by sonic waves is made of a material such as thin quartz or glass to which particles do not easily adhere, which does not generate dust, and which sonic waves penetrate well. The inner lid 402 can be detachably fixed to the open upper end of the cylindrical container 401 at a plurality of peripheral portions of the inner lid by fasteners 403. A packing 404 in the form of an O-ring made of a sealing material such as Teflon or silicon rubber to which particles do not easily adhere is provided on either the inner lid 402 or the container 401 so as to make the container 401 airtight when the inner lid 402 is closed.

On the outer surface of the inner lid 402 a filter 405 is provided for completely removing particles greater than a predetermined diameter, i.e., particles having a diameter which is larger than that of the particles to be measured. The inside and outside of the internal tank 4 are communicated through the filter 405 such that air can flow into and out of the internal tank 4 therethrough while the inner lid 402 is closed. In consequence, when air flows into the internal tank 4, particles greater than a predetermined diameter are removed by the filter 405 so as to prevent inaccurate measurement of the particles existing within the internal tank 4 which would occur as a result of dust entering from outside.

On the inner lid 402 a sampling device 410 is also provided for sampling the liquid which is contained in the internal tank 4 and which contains particles, i.e., the liquid to be measured 3. The sampling device 410 includes a sampling pipe 411 which passes through the inner lid 402 and extends substantially vertically to the vicinity of the bottom of the container 401 at one end thereof when the inner lid 402 is closed, a connecter 412 connected to the other end of the sampling pipe 411, and a valve 413 provided on the sampling pipe 411, the valve 413 being made of a material which does not easily generate dust. The connecter 412 comprises a cylindrical socket whose inner peripheral surface is threaded and which is in general retained by a holder 414 provided on the outer surface of the inner lid 402.

The driving means 5 includes a rotary table 501 on the upper surface of which the internal tank 4 is placed, a rotary shaft 502 which extends downward and substantially vertically from the central portion of the rotary table 501 until it sticks out through the bottom surface of the external tank 1, and a motor 503 connected to the lower end of the rotary shaft 502 for rotating the rotary table 501 together with the internal tank 4 through the rotary shaft 502. The gap between the rotary shaft 502 and the external tank 1 is sealed by a packing 504.

The sonic wave generating means 6 is provided on the outer peripheral surface of the external tank 1, and is composed of an ultrasonic wave oscillator 601 and a megasonic wave oscillator 602 which are mounted on adjacent outer surfaces of the external tank 1. The ultrasonic wave oscillator 601 is adapted to generate ultrasonic waves having a frequency ranging between 20 KHz and 100 KHz toward the interior of the internal tank 4 through the side walls of the external tank 1 and the internal tank 4. The ultrasonic waves which have passed through the interior of the internal tank 4 and which have penetrated the opposite side wall thereof strike a frontal reflection prevention plate 603 provided on the side wall of the external tank 1 which faces the one on which the ultrasonic wave oscillator 601 is provided in such a manner that it is inclined with respect to the oscillation surface of the ultrasonic wave oscillator 601 by a suitable angle (preferably, by an angle ranging between 3 degrees and 30 degrees), so that the waves are thereby reflected in a direction which differs from the reverse of their direction of incidence. This prevents the reflected waves from interferring with and attenuating the ultrasonic waves generated by the ultrasonic oscillator 601. The oscillation surface of the megasonic wave oscillator 602 is disposed at about a 90 degree angle to the oscillation surface of the ultrasonic wave oscillator 601, and the megasonic wave oscillator 602 is adapted to generate megasonic waves having a frequency ranging between 100 KHz and 1 MHz toward the interior of the internal tank 4 through the side walls of the external tank 1 and the internal tank 4. The megasonic waves which have passed through the interior of the internal tank 4 and which have penetrated the opposite side thereof strike a frontal reflection prevention plate 604 provided on the side surface of the internal tank which faces the side surface on which the megasonic wave oscillator 602 is provided in such a manner that it is inclined with respect to the oscillation surface of the megasonic wave oscillator 602 at a suitable angle (preferably, at an angle ranging between 3 degrees and 30 degrees), the waves being reflected in a direction which differs from the reverse of their direction of incidence. Therefore, interference and attenuation of the megasonic waves generated from the megasonic wave oscillator 602 by the reflected waves is prevented. In addition, the gap between the external tank 1 and the internal tank 4 is filled with a sonic wave transferring medium 605 such as water or other liquid which transfers sonic waves well. In this example, the oscillation surface of the ultrasonic wave oscillator 601 is disposed at about 90 degrees to that of the megasonic wave oscillator 602. However, they may be disposed such that they form an angle ranging between about 90 degrees and 180 degrees.

The motor 503 of the driving means 5, the ultrasonic oscillator 601 and the megasonic oscillator 602 are electrically connected to a power control section 801, an ultrasonic wave generating device 802, and a megasonic wave generating device 803 within a control box 8 through cables 503a, 601a and 602a, respectively. Provided on a control panel at the front of the control box 8 are a power switch 801a used to control the on/off of power supply to the motor 503, ultrasonic wave generating device 802, and megasonic wave generating device 803, a timer 801b used to control the operating time of the motor 503, ultrasonic wave generating device 802, and megasonic wave generating device 803, switches 802a and 803a used to control the on/off of the ultrasonic wave generating device 802 and megasonic wave generating device 803, adjusting knobs 802b and 803b used to change the frequency of the sonic waves generated from the ultrasonic wave generating device 802 and megasonic wave generating device 803.

The measuring means 7 has a known counter for counting dust in liquid 701. The entrance side of the liquid dust counter 701 is connected to one end of a tube 702 which is connected at the other end thereof to a connector receiver 703 mounted on the upper portion of one side surface of the container 101 of the external tank 1, while the outlet side thereof is connected to a waste liquid tank (not shown) through a tube 705 with a flow meter 704 provided thereon. The connector receiver 703 provided through the side wall of the container 101 of the external tank 1 comprises a tube which is externally threaded at the outer periphery of its end portion located within the container 101. The connector 410 can be coupled to the connector receiver 703 in an airtight fashion by threadedly engaging an internally threaded portion of the connector 412 connected to the sampling pipe 411 of the sampling device 410 with this externally threaded portion. In this way, the sampling pipe 411 can be connected to the liquid dust counter 701 through the tube 702.

A pressurized air supply system 9 for supplying pressurized air to the interior of the external tank 1 is connected to the upper portion of one side wall of the external tank 1. The pressurized air supply system 9 includes a pressurized air source 901, and a pressurized air supply tube 902 which is connected at one end thereof to the pressurized air source 901 and which passes through the upper portion of the side wall of the external tank 1 at the other end thereof. On the air supply tube 902 are provided a pressure adjusting valve 903, a pressure gauge 904, and a switch-over valve 905 such as a three-way valve which are successively disposed from the side of the pressurized air source 901 in this order. The pressure adjusting valve 903 is used to adjust the flow rate of the air supplied from the pressurized air source 901 to the interior of the external tank 1 through the pressurized air supply tube 902 so as to enable the pressure of the air in the external tank 1 indicated in the pressure gauge 904 to be adjusted. The switch-over valve 905 communicates the prssurized air source 901 with the external tank 1 so that the pressurized air can be supplied to the external tank 1 from the pressurized air source 901, or communicates the interior of the external tank 1 with ambient air when the pressure in the external tank is to be reduced. While the pressurized air source 901 is being communicated with the interior of the external tank 1 through the switch-over valve 905, the pressurized air supplied from the pressurized air source 901 to the interior of the external tank 1 flows into the interior of the internal tank 4 through the filter 405, and increases the pressure in the internal tank 4.

Next, the operation of this embodiment will be described below. First, the internal tank 4 is removed from the external tank 1, and is then moved into a clean space, e.g., to a chemical treatment draft located in a class 100 or less clean bench. The chemical treatment draft is provided with a supply port and a discharge pipe for clean water, e.g., pure water which contains 1000 particles/cc or less, each of which has a diameter of 0.1 μm or above. After the inner lid 402 has been removed by unfastening the fasteners 403 of the internal tank 4 within the chemical treatment draft, the measuring liquid 3 in the form of a clean liquid such as pure water which contains a small amount of particles is supplied into the container 401.

Subsequently, the sample 11 such as a solid is placed within the container 401, and the inner lid 402 is fixed to the open upper end of the container 401 by the fasteners 403, by which the gap between the container 401 and the inner lid 402 is sealed by the packing 404. At this time, the valve 413 of the sampling device 410 is closed. Thereafter, the internal tank 4 is returned into the external tank 1, and the sonic wave transferring medium 605 such as water is filled in the external tank 1 up to a level which exceeds the upper ends of the oscillation surfaces of the ultrasonic wave oscillator 601 and the megasonic wave oscillator 602. At this time, the switch-over valve 905 provided on the pressurized air supply tube 902 connected to the external tank 1 is switched over beforehand so that the interior of the external tank 1 does not communicate with the pressurized air source 901 but with ambient air. Also, the connector 411 connected to one end of the sampling pipe 411 is held by the holder 414 provided on the inner lid 402 of the internal tank 4 and is not connected to the connector receiver 703 connected to one end of the tube 702, which means that the sampling tube 411 is not communicated with the liquid in the dust counter 701. After the above-described items have been confirmed, the outer lid 103 of the external tank 1 is fixed to the open upper end of the container 101 by the fastener 105.

Subsequently, the processing time, i.e., the operating time, of the motor 503, ultrasonic wave generating device 802 and megasonic wave generating device 803 is set using the timer 801b on the control panel 804 of the control box 8, and the motor 503, the ultrasonic wave generating device 802 and the megasonic wave generating device 803 are then actuated by turning on the power switch 801a. As the ultrasonic wave generating device 802 and the megasonic wave generating device 803 are actuated, ultrasonic and megasonic waves are respectively generated from the ultrasonic wave oscillator 601 and the megasonic wave oscillator 602, and the generated ultrasonic and megasonic waves penetrate the side wall of the external tank 1, the sonic wave transferring medium 605, then through the side wall of the internal tank 4 to reach the sample 2 accommodated within the internal tank 4 and wash away the particles attached to the surface thereof. In other words, dust having a relatively large diameter, e.g., dust having a diameter of 1 $\mu$m to 10 $\mu$m, is removed from the sample 2 by the impacting force of cavitation caused by the ultrasonic waves, while dust having a relatively small diameter, e.g., dust having a diameter of 0.1 $\mu$m to 1 $\mu$m, is removed from the sample 2 by the fierce impact of the megasonic waves on the contacted surfaces of the sample 2 and the dust adhered thereto. During this time, the internal tank 4 is rotated at a relatively low speed of about 20 to 50 rpm by the motor 503 so that sonic waves such as ultrasonic and megasonic waves strike the surfaces of the sample 2 evenly. Further, since the container 401 of the internal tank 4 is formed into a cylindrical shape using a thin material which sonic waves penetrate well, e.g., glass having a wall thickness of 2 mm to 5 mm, the sonic waves are not attenuated when they penetrate the side wall of the internal tank 4, and they strike the sample 2 evenly. Further, since the sonic waves which have passed through the internal tank 4 strike the frontal reflection prevention plates 603 and 604 disposed on the side surfaces of the external tank 1 which face the side surfaces on which the ultrasonic wave oscillator 601 and the megasonic wave oscillator 602 are provided, and are reflected in a direction which differs from the reverse of their direction of incidence, interference of the incident waves with the reflected waves is eliminated, thereby preventing attenuation of the incident waves. Thus, the dust attached to the surface of the sample 2 is substantially removed therefrom in a very efficient manner and is diffused in the measuring liquid 3.

After a predetermined processing time has elapsed, i.e., after the time set by the timer 801b has elapsed, the outer lid 103 of the external tank 1 is opened, and the connector 411 of the sampling pipe 411 which has been held by the holder 414 of the inner lid 402 of the internal tank 4 is connected to the connector receiver 703 mounted on the external tank 1. Thereafter, the valve 413 is opened, and the outer lid 103 is again closed.

Then, the pressure of the pressure adjusting valve 903 is set to a value ranging between 0.5 kg/cm$^2$ and 2 kg/cm$^2$, and the switch-over valve 905 is switched over for supply of the pressurized air, by means of which the pressurized air is supplied through the pressurized air supply tube 902 to the interior of the external tank 1, then to the interior of the internal tank 4 through the filter 405 so as to pressurize the particle containing liquid, i.e., the measuring liquid 3, in the internal tank 4 thereby enabling part thereof to be transferred as a sample to the liquid dust counter 701 through the sampling pipe 411 and the tube 702. The sample is then discharged from the liquid dust counter 701 to the waste water tank (not shown) through the flow meter 704 and the tube 705. The rate at which the particle containing liquid flows into the liquid dust counter 701 is adjusted by rotating a knob 704a of the flow meter 704. After the flow rate of the liquid supplied to the liquid dust counter 701 has been adjusted to a fixed value in the manner described above, the quantity of particles contained in the measuring liquid 3 is determined by the dust counter 701. More specifically, in the known liquid dust counter 701, light, such as visible light, ultraviolet light or a laser beam, having a fixed wavelength is irradiated on the particle containing liquid from the light source (not shown), and the light which has been scattered by the particles contained in the liquid is received by a light receiving means (not shown) so as to measure the intensity of light scattered and thereby count the number of particles.

In the above-described embodiment, the particle containing liquid in the internal tank 4 is transferred to the dust counter 701 using pressurized air which is supplied by the pressurized air supplying system 9 including the pressurized air supply pipe 902, the pressure adjusting valve 903, the pressure gauge 904, and the switch-over valve 905. However, a pump which is capable of sucking a fixed amount of liquid may also be used. In that case, the pump is connected to the tube 705 leading to the outlet of the liquid dust counter 701.

Figure 4:
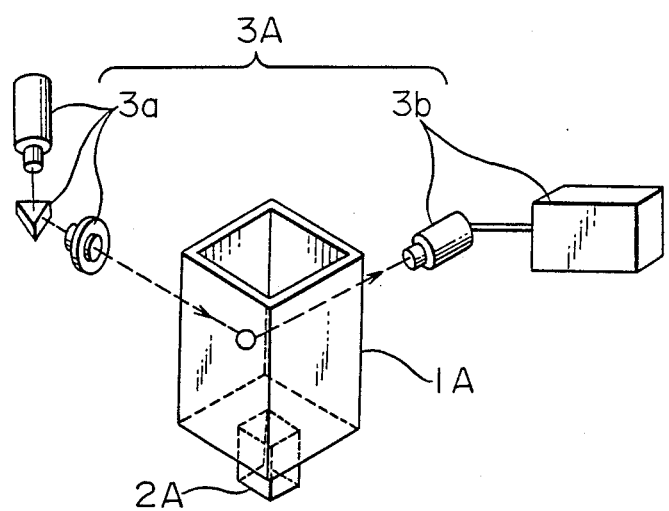
FIG. 4 is a perspective view of a known apparatus for counting particles attached to the surface of a solid.

As will be understood from the foregoing description, in the present invention, sonic waves having a plurality of different frequencies generated from the sonic wave generating means provided on the external tank are irradiated on the overall surfaces of the sample uniformly by rotating the internal tank with respect to the external tank by the driving means so as to wash away almost all of the particles attached to the surfaces of the sample in the measuring liquid contained in the internal tank. In consequence, particle size distribution of the particles attached to thee surface of the sample can be faithfully reproduced in the measuring liquid, and the accuracy with which the particles are counted can be thereby improved to a large extent as compared with the known counting apparatus as shown in FIG. 4. Further, removal and washing away of the particles from the solid surface can be conducted within the sealed internal tank, and the measuring liquid containing the removed particles can be transferred to the measuring means without being exposed to ambient atmosphere, where the number of particles are counted. Therefore, contamination by dust or foreign particles of the measuring liquid can be avoided, resulting in a substantial improvement in the reliability of measurement.

What is claimed is:

1. An apparatus for counting particles attached to surfaces of a solid comprising: an external tank; an internal tank disposed within said external tank, said internal tank being capable of hermetically accommodating a measuring liquid into which a sample having particles attached to the surfaces thereof is to be immersed, a driving means for rotating said internal tank with respect to said external tank, a sonic wave generating means for generating sonic waves having a plurality of different frequencies toward said internal tank, and a measuring means connectable to said internal tank in a hermetic fashion for counting the number of particles in the measuring liquid that have been removed from said sample by the sonic waves generated from said sonic wave generating means.

2. An apparatus for counting particles attached to surfaces of a solid according to claim 1, wherein said internal tank is made of a material to which particles do not easily adhere and which does not easily generate dust, in particular, a portion of said internal tank on which sonic waves are irradiated being made of a material to which particles do not easily adhere, which does not easily generate dust and which sonic waves penetrate well.

3. An apparatus for counting particles attached to surfaces of a solid according to claim 2, wherein said material to which particles do not easily adhere and which does not easily generate dust is a one selected from quartz, glass, silicone, Teflon, SUS and polymeric polypropylene.

4. An apparatus for counting particles attached to surfaces of a solid according to claim 2, wherein said material to which particles do not easily adhere, which does not easily generate dust and which sonic waves penetrate well is a thin quartz or glass.

5. An apparatus for counting particles attached to surfaces of a solid according to claim 1, wherein said internal tank comprises a cylindrical container having an open end and a closed end, an inner lid removably mounted on the open end of said container, a fastener for fixing said inner lid to said cylindrical container when said inner lid is closed, and a packing provided between the open end of said container and said inner lid for sealing the gap therebetween when said inner lid is closed.

6. An apparatus for counting particles attached to surfaces of a solid according to claim 1, wherein said external tank comprises a box-shaped container having an opening, an outer lid mounted on said container for closing and opening of said opening, a fastener for fixing said outer lid to said box-shaped container when said outer lid is closed, and a packing provided between said open end of said box-shaped container and said outer lid for sealing the gap therebetween when said outer lid is closed.

7. An apparatus for counting particles attached to surfaces of a solid according to claim 1, wherein said sonic wave generating means comprises an ultrasonic wave generating source and a megasonic wave generating source.

8. An apparatus for counting particles attached to surfaces of a solid according to claim 7, wherein said ultrasonic wave generating source generates ultrasonic waves having a frequency ranging between 20 KHz and 100 KHz, and said megasonic wave generating source generates megasonic waves having a frequency ranging between 100 KHz and 1 MHz.

9. An apparatus for counting particles attached to surfaces of a solid according to claim 7, wherein said ultrasonic wave generating source and said megasonic wave generating source respectively have oscillation surfaces disposed at an angle of 90 degrees to 180 degrees with respect to each other.

10. An apparatus for counting particles attached to surfaces of a solid according to claim 7, further including frontal reflection prevention plates provided on the side surfaces of said external tank which face the side surfaces on which said ultrasonic wave generating source and said megasonic wave generating source are provided in such a manner that they are inclined with respect to the corresponding oscillation surfaces of said ultrasonic and megasonic generating sources, said frontial reflection prevention plates being adapted to reflect sonic waves irradiated from said generating sources in directions which differ from the reverse of their directions of incidence.

11. An apparatus for counting particles attached to surfaces of a solid according to claim 1, wherein a gap between said internal tank and said external tank is filled with a sonic wave transferring medium.

12. An apparatus for counting particles attached to surfaces of a solid according to claim 1, wherein said driving means comprises a rotary table on the upper surface of which said internal tank is placed, a rotary shaft which extends downward and substantially vertically from the central portion of said rotary table to pass through the bottom surface of said external tank in an airtight fashion, and a motor connected to the lower end of said rotary shaft.

13. An apparatus for counting particles attached to surfaces of a solid according to claim 1, wherein said measuring means is a dust counter for counting particles of dust in a liquid.

14. An apparatus for counting particles attached to surfaces of a solid according to claim 5, wherein said measuring means is capable of being communicated with said internal tank through a sampling device.

15. An apparatus for counting particles attached to surfaces of a solid according to claim 14, wherein said sampling device has a sampling pipe which passes through said inner lid and extends at one end thereof to the vicinity of the bottom of said cylindrical container at one end thereof when said inner lid of said internal tank is closed, a connector connected to the other end of said sampling pipe, said connector being detachably coupled to a connector receiver provided at and extending through the upper portion of said external tank, said connector receiver being connected to said measuring means through a tube, and a valve provided on said sampling pipe.

16. An apparatus for counting particles attached to surfaces of a solid according to claim 15, wherein the interior of said internal tank communicates with said external tank through a filter.

17. An apparatus for counting particles attached to surfaces of a solid according to claim 16, further comprising a pressurizing means connected to the upper portion of said external tank for pressurizing the interior thereof by supplying pressure air to the interior of said external tank.

18. An apparatus for counting particles attached to surfaces of a solid according to claim 17, further comprising a flow-rate adjusting mechanism provided downstream of said measuring means for adjusting the sampling flow rate of the particle-containing measuring liquid which flows into said measuring means from said internal tank.

19. An apparatus for counting particles attached to surfaces of a solid according to claim 16, further comprising a pump connected with said measuring means for sucking the liquid from said internal tank into said measuring means.

* * * * *